United States Patent
León Carrera et al.

(10) Patent No.: US 10,656,068 B2
(45) Date of Patent: May 19, 2020

(54) METHOD FOR PROVIDING A NUMERICAL MODEL OF A SAMPLE OF ROCK

(71) Applicant: REPSOL, S.A., Madrid (ES)

(72) Inventors: María Fernanda León Carrera, Madrid (ES); Almudena Diáz Aguado, Madrid (ES); Noelia Rodríguez Morillas, Madrid (ES); Laurent Fontanelli, Madrid (ES)

(73) Assignee: REPSOL, S.A., Madrid (ES)

( * ) Notice: Subject to any disclaimer, the term of this patent is extended or adjusted under 35 U.S.C. 154(b) by 229 days.

(21) Appl. No.: 15/763,176

(22) PCT Filed: Oct. 2, 2015

(86) PCT No.: PCT/ES2015/070719
§ 371 (c)(1),
(2) Date: Mar. 26, 2018

(87) PCT Pub. No.: WO2017/055647
PCT Pub. Date: Apr. 6, 2017

(65) Prior Publication Data
US 2018/0321127 A1   Nov. 8, 2018

(51) Int. Cl.
*G06K 9/00* (2006.01)
*G01N 15/08* (2006.01)
*G01N 33/24* (2006.01)
*G01N 23/046* (2018.01)
*G01V 99/00* (2009.01)

(52) U.S. Cl.
CPC ........... *G01N 15/08* (2013.01); *G01N 23/046* (2013.01); *G01N 33/24* (2013.01); *G01N 2015/0846* (2013.01); *G01N 2223/401* (2013.01); *G01N 2223/616* (2013.01); *G01N 2223/649* (2013.01); *G01V 99/005* (2013.01)

(58) Field of Classification Search
None
See application file for complete search history.

(56) References Cited

U.S. PATENT DOCUMENTS

| | | | |
|---|---|---|---|
| 2003/0173072 A1* | 9/2003 | Vinegar | B09C 1/02 166/66.5 |
| 2013/0262028 A1 | 10/2013 | De Prisco et al. | |
| 2014/0270394 A1 | 9/2014 | Fredrich et al. | |
| 2015/0062300 A1 | 3/2015 | Li et al. | |
| 2017/0074773 A1* | 3/2017 | Gulli | G01N 15/0826 |
| 2018/0031732 A1* | 2/2018 | Mosse | G01V 99/005 |
| 2018/0106708 A1* | 4/2018 | Siebrits | G01N 23/046 |

OTHER PUBLICATIONS

International Search Report for International Application No. PCT/ES2015/070719 dated Jun. 28, 2016, 10 pages.

* cited by examiner

*Primary Examiner* — Wei Wen Yang
(74) *Attorney, Agent, or Firm* — Reising Ethington, P.C.

(57) ABSTRACT

The present invention relates to a method for providing a numerical model of a sample of rock that, when used for flow simulations, it reproduces the porosity and the permeability according to the measurements taken in said sample of the rock. The method is characterized in that the structure and the properties of the numerical model are populated randomly ensuring that the global behavior reproduces the measurements.

13 Claims, 3 Drawing Sheets

METHOD FOR PROVIDING A NUMERICAL MODEL OF A SAMPLE OF ROCK

RELATED APPLICATION

This application is the National Stage of International Patent Application No. PCT/ES2015/070719, filed on Oct. 2, 2015.

OBJECT OF THE INVENTION

The present invention relates to a method for providing a numerical model of a sample of rock that, when used for flow simulations, it reproduces the porosity and the permeability according to the measurements taken in said sample of the rock.

The method is characterized in that the structure and the properties of the numerical model are populated stochastically ensuring that the global behavior reproduces the measurements.

BACKGROUND OF THE INVENTION

Rock and its properties can be determined with the help of images data. Photographs can be a good assist in rock mass classification, first by allowing zones with different patterns to be identified and the boundaries between them defined and secondly by allowing the distribution of block sizes and shapes.

In the last decade, the industry has developed methods for characterizing carbonate rocks at microscopic scale using Confocal microscopy, Micro-/Nano-X-ray Computed Tomography (CT), Focused Ion Beam-Scanning Electron Microscopy (FIB-SEM) or at macroscopic scales using CT scan technology and ordinary microscopy methods. These methodologies allow studying digital data and analyzing the distribution of the pore network in three dimensions, in order to determine petrophysical properties. Great emphasis has been placed on these techniques to determine the storage capability and flow of rock cores. However, it is needless to say that such capabilities are affected by components constituting the rock and that the distribution of the components affects the petrophysical properties.

Density appears to be an easy concept to understand. At its most basic definition, it is a very simple and straight forward concept. Simply divide the mass of an object by the volume. However, when it comes time to start adding in additional factors like porosity, permeability, absorption rates, pore sizes, and the processes that form the samples themselves things can easily become complicated. Most things in the geotechnical engineering world do not fall in perfect geometric shapes, so the ability to accurately assess the volume of a sample is vital.

Traditional methods for estimating size and porous distributions are indirect therefore they can be inaccurate carrying out measurement errors. Measurements from photographs or formation microimager have relied on counting only the wholly visible fragments, ignoring the ones overlapped by other particles, giving a serious sampling bias.

Hydraulic conductivity of the rock mass depends on spacing and connectivity of the network of joints, and on the roughness and apertures of each individual joint. To understand the fluid behavior and the rock interactions, the evolution of physical and morphological characteristics of connected space and the rock walls have to be modelled.

In situ rocks need to be viewed from several directions to adequate sample a 3D pattern. The CT scan provides a measurement of the attenuation of the radiation of the X-ray in certain volume or the whole volume of a plug sample of rock. The CT scan provides a 3D representation of the scanned object wherein said representation is a 3D image described by voxels.

A voxel represents a value on a regular grid in three-dimensional space wherein said voxel is often represented by a parallelepiped. The set of voxels of the 3D image are a discretization of the volume that has been scanned and the color value of the image may represent a scalar function defined in said discretization. CT scan, as it will be used along this description, provides a gray scale and the gray value represents the value (scalar value) of the measurement of the attenuation of the radiation in a range. The gray value will be used as a measurement, a measurement of the attenuation of the radiation of the X-ray, taken from the sample at each point of the discretization defined by the 3D image.

The CT scan does not provide absolute values of physical properties such as the density, just gray values that may be qualitatively assessed by an expert. These 3D images are very useful for the understanding of the structure of the sample of rock scanned but, even if the measurement of the attenuation of the radiation is proportional to the density, the image is not a measurement of the density. For instance, when a CT scan scans twice the same sample of rock, the second measurement differs from the first one due to the CT scan works under different conditions and the gray values cannot be interpreted as absolute measurements of the density.

Because the above identified limitations, physical properties such as density, porosity and permeability, cannot be characterized by CT scan techniques.

The discretization of the 3D image provided by a CT scan is not a numerical model of a sample of rock as it lacks of the structural properties reproducing the behavior of the sample of rock.

The measurements of porosity may be carried out in a lab for instance to obtain the total porosity of the sample of rock. The same applies to the measurement of the permeability wherein the permeability is measured by forcing a flow across the sample of rock in a predetermined direction and under certain conditions. These measurements highly depend on the internal structure and properties of the rock but they do not provide data to allow disclosing the internal structure of the sample of rock.

For instance, the fluid may easily flow because the high permeability of the whole sample of rock or because, even if the permeability of the whole sample of rock is low, the existence of a fracture defines a path for the flow with a very low resistance to the flow. A numerical model must comprise an internal structure providing the same flow behavior than the physical sample of rock.

The internal structure of a rock can be divided by facies. Each facies is determined by the same spatial relation and internal characteristic such as lithology and sedimentary structures.

Numerical simulations of reservoirs need characterizing properties of facies mainly according to the porosity and permeability properties in order to be able to simulate the behavior in the entire domain. The proposed numerical model determines the physical properties, including porosity and permeability, of a sample of rock from an oil or gas reservoir. The sample of rock, called plug sample, is extracted and analyzed from a vertical or horizontal portion of the core. The core is a sample of the reservoir formation extracted from a well according to its longitudinal direction.

If an oil or gas reservoir comprises a plurality of facies, at least one sample of rock is taken for each facies. According to a first aspect of the invention, a numerical model for each facies allows to model separately each facies. According to an embodiment of the present invention, the plurality of numerical models are used for generating a further numerical model of a core comprising a plurality of facies, being said core extracted from a well.

The problem solved by the invention is a numerical model that determines the physical properties of the sample of rock such that, when the numerical model is used to populate the properties in a certain domain, for instance in a facies or in the complete sample extracted from the well, the flow behavior of the numerical model or the flow behavior of the populated domain are according to the measurements taken from the sample of rock.

DESCRIPTION OF THE INVENTION

A first inventive aspect is a method for providing a numerical model of a sample of rock. In particular, the sample of rock may be a plug sample taken from, as an example, a portion of the vertical core extracted from a well in an oil or gas reservoir. In this case the plug is taken from a single facies. Hereinafter, the term "plug" will be used as synonymous of sample of rock.

The method comprises the following steps:
carrying out a CT scan of the plug sample of rock,
measuring the porosity $\phi_m$, of the plug sample of rock by an experiment,
measuring the permeability $k_{ms}$ of the plug sample of rock by an experiment.

As it is know from the prior art, these methodologies allow to study qualitatively digital data and to analyze the distribution of the pore network in three dimensions. Those capabilities are affected by components constituting the rock and wherein the distribution of the components affects the petrophysical properties.

The spatial organizations of the components that contribute to the pore network may be analyzed. The process, analysis and interpretation of CT scan images allow the validation of the representativeness of the plug samples and their main components. These tasks may be carried out by a skilled person in the art.

However, according to the invention, these methodologies will be used for obtaining a detailed 3D numerical model of a sample of rock. The first step is the characterization of the sample of rock using CT scan technology. The CT scan provides a 3D image which can be used to provide a discretization of the sample of rock for the numerical model. That is, the image comprises voxels that are interpreted as the discretization of certain volume or the whole volume of the sample of rock.

According to the invention, a first proposal of the 3D image and therefore the discretization is generated for instance by means of a CT scan at a high resolution. Laboratory measurements, that it, the porosity $\phi_m$, measurement and the permeability $k_{ms}$ measurement, will be used for generating specific scalar distributions to the numerical model providing the same behavior as the sample of rock.

Porosity is created using laboratory measurements. The porosity value, obtained from the sample of rock, is a scalar value that corresponds to the total porosity of the sample. This porosity value can be obtained by any of the available methods. As an example, the pore volume of the sample of rock is filled with a low viscosity fluid. The volume of the fluid filling the pore volume of the sample provides a measurement for the porosity.

The permeability value is a scalar that corresponds to the total permeability measured in one direction. For example, in a cylindrical sample, the permeability corresponds to the longitudinal direction of the sample. Most of the samples are cylindrical and the longitudinal directions of these specific samples are the axis of the cylinder.

According to this first aspect of the invention, a plurality of 3D models is iteratively generated using statistical random methods wherein each model is simulated and compared to laboratory results or measurements. The method converges when the generated 3D model and the modeled values for the porosity $\phi_{num}$ and permeability $k_{num}$ reproduce at least both laboratory measurements, porosity $\phi_{ms}$ and permeability $k_{ms}$.

The method according to the invention for carrying out the iterative process, it also comprises:
generating a 3D numerical model, at least comprising a cell discretization representing the volume of the plug sample of rock, according to the following steps:
a) Recovering data from the CT scan providing at least information on the statistical density function $f(\rho)$ of the value $\rho$, wherein $\rho$ is the attenuation of the X-rays radiation in the volume of the plug sample of rock,
b) generating a segmentation of the discretization of the first 3D model into sub-volumes responsive to the data retrieved in step a) from the plug sample of rock, said sub-volumes representing components of the plug sample of rock.

As it has been disclosed, the CT scan provides a 3D image comprising voxels and a scalar value that may be represented by gray colors. The gray colors are interpreted as a scalar value responsive to the density as the density is proportional to the attenuation of the X-rays radiation $\rho$. The porosity $\phi$ is calculated as the normalized value $\rho'$, being $\rho'$ the normalized value $|-\rho|$ (ranging [0, 1] scaled from a predetermined minimum reference value and a predetermined maximum reference value defined from a calibration procedure) of the attenuation of the X-rays radiation of the CT scan. The volume that has been scanned is discretized for instance using the voxels of the image as the discrete cells of the volume being scanned. According to an embodiment, the predetermined minimum reference value and the predetermined maximum value are the minimum and the maximum value respectively of the read measurements obtained from the CT scan.

Using the discretization defined by the 3D image is very efficient; however, according to an embodiment, a different discretization with density values obtained by interpolation of the values of the 3D image allows to adjust the resolution of the numerical model.

The sample of rock is taken from a single facies but it may contain more than one component.

These components, according to the prior art, are identified by a skilled person in the art by interpreting the gray scale image of the CT scan and maybe using additional information. Different components with different densities appear as regions having gray scales within different ranges.

According to the present invention, a segmentation of the first 3D model into sub-volumes responsive to the data retrieved in step a) provides a proposal of the statistical distribution of the components in the volume. This proposal may differ from the real distribution as it depends on the segmentation process. The segmentation of the discretization of the first 3D model may be carried out by using any of the well-known algorithms for segmenting a domain responsive to a scalar value.

According to an embodiment of the invention, when the iterative method does not converge to a 3D numerical model reproducing the measurements for the porosity and the permeability, the segmentation is repeated using a different criteria used previously or a different algorithm providing a different sub-volume distribution.

c) Identifying the components of each sub-volume.

Once the volume representing the sample of the rock has been discretized and segmented, each sub-volume is identified as a rock component. In this step, the range of the attenuation of the X-rays radiation ρ may allow to identify each component. In some embodiments, additional information such as the natural radiation or additional measurements in the sample of rock may be used in order to identify one or more components.

The integrating data from laboratory analysis and CT scan image generate the porosity and permeability models by using the Gaussian simulation methods by components that contribute to the flow as it will be further disclosed.

d) Determining a porosity statistical distribution function $F(\phi)$ for the cells of the 3D model at least responsive to the statistical density function $f(\rho)$.

The CT scan measurements provide information on the statistical density function $f(\rho)$ of the value ρ of the attenuation of the radiation of the X-rays in the volume of the plug sample of rock. The attenuation of the radiation does not distinguish variations due to the combination of different materials having the same density or when the porosity compensates a higher density. In this case, the combination of the value ρ of the attenuation of the radiation of the X-rays and additional information, for instance information retrieved from the natural radiation allows to distinguish among a plurality of components.

According to an embodiment, the porosity statistical distribution function is determined directly from the statistical density function $f(\rho)$ wherein components contributing to porosity and components no contributing to porosity are distinguished.

A further embodiment retrieves additional information from each component; for instance by a query to a data base, that may be used to modify the proposed porosity statistical distribution function $F(\phi)$.

A specific method according to an embodiment for determining the porosity statistical distribution function will be disclosed in the detailed description of the invention.

e) Populating the porosity ϕ for each sub-volume of the 3D model, wherein the porosity is spatially distributed among the cells of said sub-volume by means of a Gaussian simulation algorithm responsive to the porosity statistical distribution function $F(\phi)$ as an approximation of a Gaussian density function.

f) Populating the permeability among the cells of each sub-volume comprising a component contributing to the porosity, wherein the permeability is defined as a scalar function responsive of the porosity of the cell $k(\phi)$.

g) Performing a numerical simulation of the 3D model according to the conditions of the experiment performed to obtain the permeability $k_{ms}$ in order to obtain its global permeability $k_{num}$.

h) Iteratively repeating steps e) to g) until the global permeability measured on the plug sample of rock $k_{ms}$ and the permeability $k_{num}$ calculated from the 3D model differ less than a pre-specified threshold, making the first 3D numerical model available.

The porosity statistical distribution function $F(\phi)$ at step e), according to an embodiment, is determined as follows:

determining $\Delta CT_1=|CT_{mean}-CT_{min}|$ and $\Delta CT_2=|CT_{max}-CT_{mean}|$ as the ρ values ranges from $CT_{min}$ to $CT_{max}$, and the statistical density function $f(\rho)$ has a mean value at $CT_{mean}$;

being $\Delta\phi_1=|\phi_{mean}-\phi_{min}|$ and $\Delta\phi_2=|\phi_{max}-\phi_{mean}|$ wherein $\phi_{min}$ is the minimum value of the porosity ϕ, $\phi_{max}$ is the maximum value of the porosity ϕ; and, $\phi_{mean}$ is the mean value of the porosity statistical distribution function $F(\phi)$ fixed as the measured porosity $\phi_{ms}$;

provide the porosity statistical distribution function $F(\phi)$ as the symmetric function of the statistical density function $f(\rho)$ of the value ρ, scaled and shifted such as:

$$\frac{\Delta\phi_2}{\Delta\phi_1} = \frac{\Delta CT_1}{\Delta CT_2}$$

Probability function distribution describes the spread of a random variable that is used to estimate the probability of the occurrence of a parameter value. It has typical and unique properties of distribution that make one function different from others. For the sake of clarity, the statistical density function has been normalized as ρ' where the porosity values are defined between 0 and 1. However, a plurality of scalar distributions within a domain provides the same probability function distribution. Two different scalar distributions of the permeability according to the same probability function provide different numerical models with a behavior of the global permeability that are different. Because of this fact, a skilled person would not use a statistical method for populating scalar variable in order to obtain a representative numerical model as it does not ensures the behavior of the sample of rock.

According to the invention, a plurality of numerical samples is generated by populating the porosity and the permeability according to steps e) and f) respectively along the entire numerical domain, at least for the components contributing to the porosity, and said numerical samples are simulated according to step g) under the conditions stated by the measurements.

When a generated numerical sample, being simulated under the same conditions than those used for the measurements carried out on the sample of rock, shows a global permeability and a permeability that differs less than a pre-specified threshold from the measurement then said generated numerical sample is provided as the 3D numerical model of the sample of rock.

Fixing a pre-specified threshold for carrying out the method is an ordinary task for the skilled person according to the measurements obtained in the laboratory.

As the porosity and the permeability scalars of the 3D numerical model are randomly generated for each component, the distribution is not the same as the distribution of the sample of rock but the behavior of said 3D numerical method in respect of both variables, the porosity and the permeability, is deemed to be the same.

DESCRIPTION OF THE DRAWINGS

The foregoing and other features and advantages of the invention will be more clearly understood based on the following detailed description of a preferred embodiment provided by way of illustrative and non-limiting example in reference to the attached drawings.

DETAILED DESCRIPTION OF THE INVENTION

Figure 1:
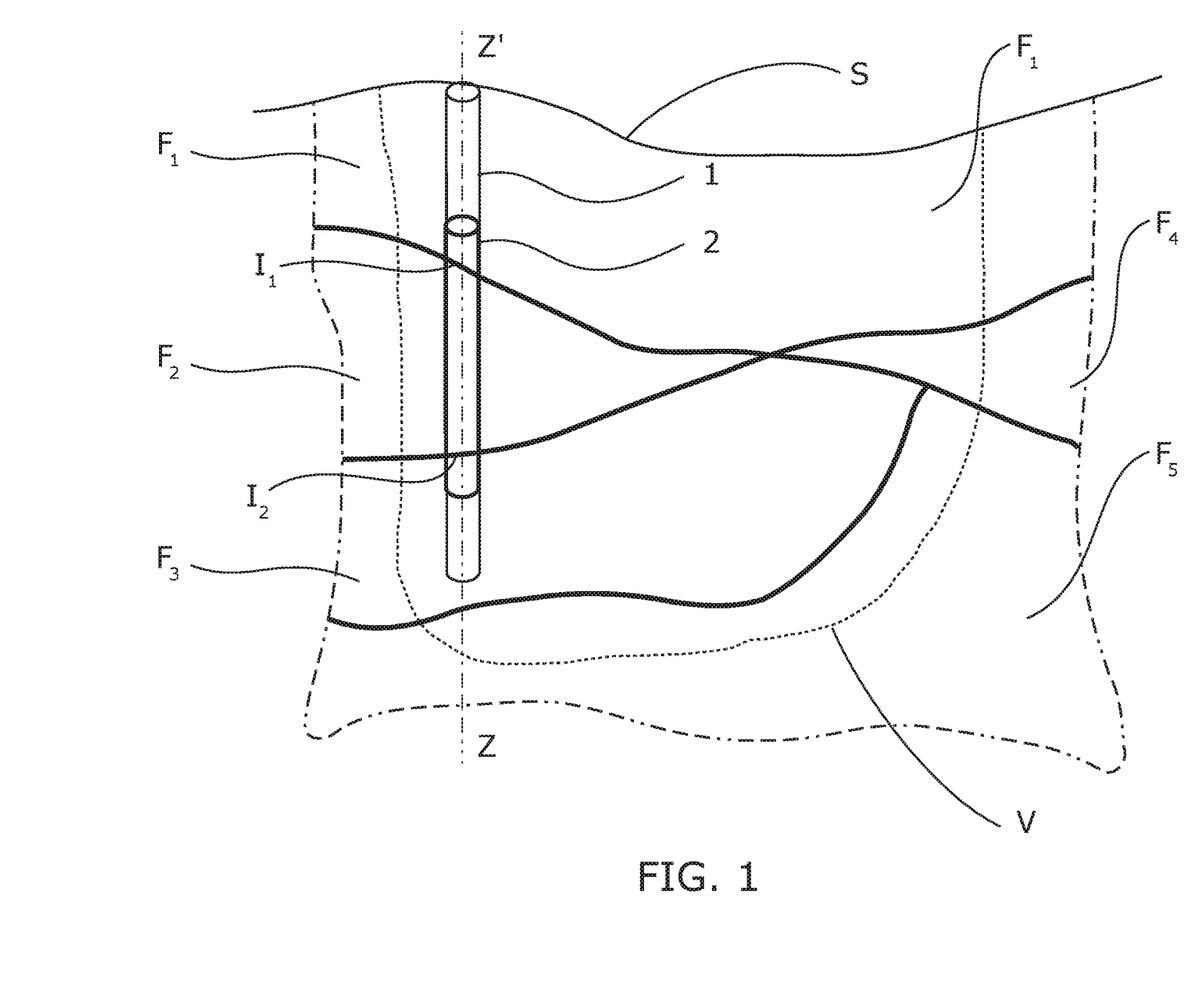
FIG. 1 This figure shows a schematic representation of a sectional view of a reservoir located under the surface to be explored.

A detailed description of the invention is disclosed wherein the invention is used over a particular reservoir as it is shown in the schematic sectional view in FIG. 1. The reservoir is limited by a surface (S) that is being explored using methods for retrieving limited data from the subsoil.

Wells (1) are a common practice for retrieving data from the subsoil. The well (1) provides a large sample of rock (2) along the vertical direction Z-Z', shown as a dashed line, at certain location on the surface (S) to be explored.

Numerical models of the reservoir are built by discretizing certain volume (V) under the surface (S) to be explored and, soil properties must be defined in the numerical model. Such discretization and the equations involved in modeling the volume (V), being V the numerical domain, are chosen depending on the facies located within the volume (V) and its properties.

During this process, the large sample of rock (2) obtained from the well (1) is used for retrieving valuable information for defining facies ($F_1$, $F_2$, $F_3$, $F_4$, $F_5$) and the physical properties of the components.

According to an embodiment of the present invention, a 3D numerical model of the large sample of rock (2) obtained by drilling along the vertical direction Z-Z' will be generated in a two steps method, a first step provides numerical models of plugs extracted from each facies ($F_1$, $F_2$, $F_3$, $F_4$, $F_5$) and a second step populates said numerical models to the entire domain of the sample of rock (2).

In this example, the large sample of rock (2), the core, after the extraction is qualitatively analyzed by a skilled person, for instance by using a CT scan. The 3D image of the CT scan allows the skilled person to identify facies ($F_1$, $F_2$, $F_3$) and regions of different components. Additional laboratory experiments, such as measurement of natural radiation, provide a more accurate qualitative description of the large sample or rock.

Figure 2:
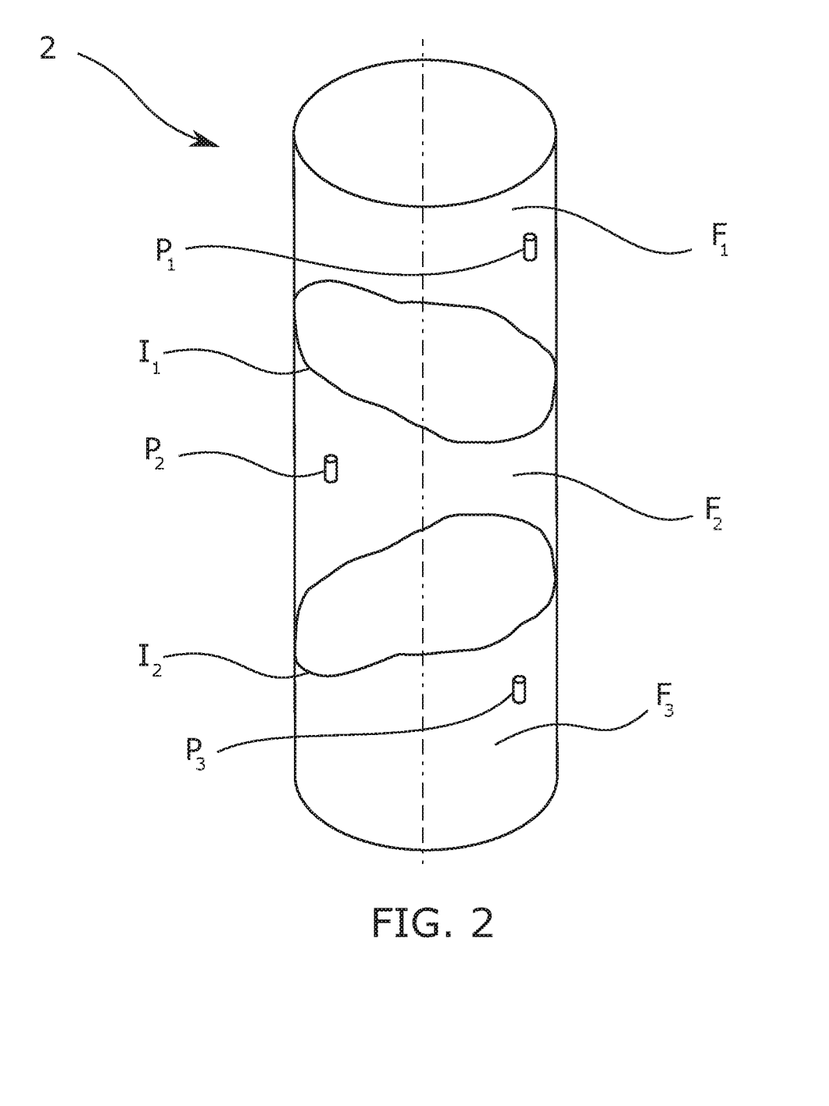
FIG. 2 The figure shows the sample of rock extracted from the well with several facies corresponding to the facies of the reservoir; and, it also shows plug samples taken from each facies of said sample of rock.

FIG. 2 shows the sample of rock (2) extracted from the well (1) with three facies ($F_1$, $F_2$, $F_3$) corresponding to the structure of the underground facies ($F_1$, $F_2$, $F_3$, $F_4$, $F_5$), each facies ($F_1$, $F_2$, $F_3$) separated by an interface identified as $I_1$ and $I_2$.

This qualitative description is used for obtaining plugs ($P_1$, $P_2$, $P_3$), small samples of rock from each facies ($F_1$, $F_2$, $F_3$) previously identified.

According to the first aspect of the invention, for each plug ($P_i$, i=1 ... N, being N the total number of facies) a 3D numerical model is built wherein said 3D numerical models, according to an embodiment, will have a high resolution discretization of the volume of the plug; that is, the numerical model comprises a large number of cells in order to provide an accurate model of the sample of rock.

A laboratory measurement is carried out over the plug, wherein a low viscosity fluid, usually helium or nitrogen, is injected into the plug wherein the injected volume determines the porosity value $\phi_{ms}$ of the plug.

A second one is carried out over the same plug in order to obtain the permeability $k_{ms}$ along a certain direction. In this embodiment the plug has a cylindrical shape and the direction is the longitudinal. The plug is closed in its lateral wall. Then, a fluid is injected into one of the circular surfaces at certain pressure in respect to the pressure at the opposite circular surface. The differential pressure imposes a flow which is driven in the longitudinal direction of the plug with an internal configuration of the velocity field depending on the porosity and the permeability of said plug. The total flow provides a measurement of the permeability of the plug $k_{ms}$.

A CT scan of the plug provides a gray scale image and the voxels of the image provides a discretization of the plug. In this embodiment, the discretization of the image is used as the discretization of the numerical model of the plug.

The image, according to this embodiment, is used for clustering the discretization according to the components of the plug by means of a segmentation algorithm and, those clusters identified with components not having porosity will not be used for propagating the porosity and the permeability reducing the computational cost of the simulations that will be carried out at a later stage.

Figure 3A:
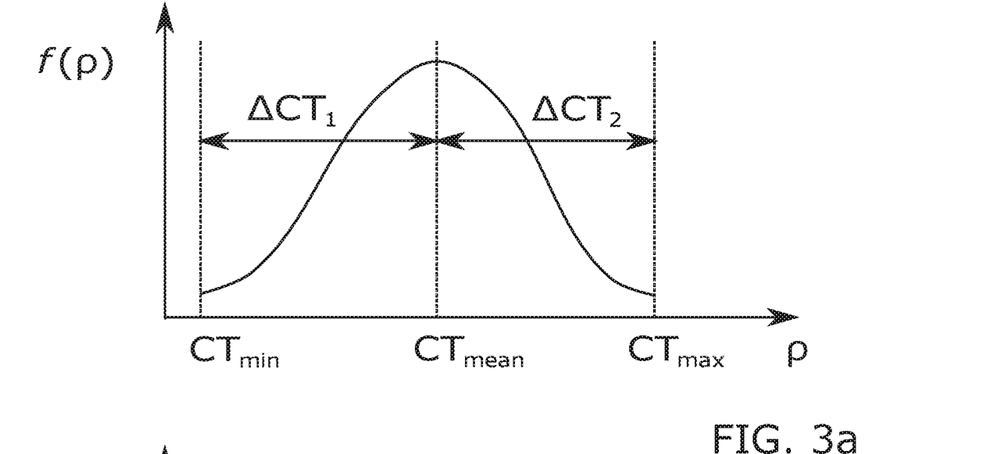
FIG. 3a, 3b, 3c FIGS. 3a, 3b and 3c show three functions, the statistical density function $f(\rho)$ obtained from the CT scan, the porosity density function $F(\phi)$ obtained from $f(\rho)$ and the truncated statistical density function $f_c(\rho)$.

The CT scan provides information related to the porosity of the plug as the attenuation of the X-rays radiation is inversely proportional to the density of the component. FIG. 3a shows the statistical density function of the CT scan measurement, $f(\rho)$. The CT scan statistical density function ranges between $CT_{min}$ and $CT_{max}$, and a mean value $CT_{mean}$ is calculated from $f(\rho)$ therefore it is a known value.

As it has been indicated, the CT scan statistical density function is related with the porosity function. Therefore the $CT_{mean}$ value is equal to the experimental porosity measurement $\phi_{ms}$.

As disclosed, the porosity statistical distribution function $F(\phi)$ at step e) is determined as follows:
- determining $\Delta CT_1 = |CT_{mean} - CT_{min}|$ and $\Delta CT_2 = |CT_{max} - CT_{mean}|$ as the $\rho$ values ranges from $CT_{min}$ to $CT_{max}$, and the statistical density function $f(\rho)$ has a mean value at $CT_{mean}$;
- being $\Delta\phi_1 = |\phi_{mean} - \phi_{min}|$ and $\Delta\phi_2 = |\phi_{max} - \phi_{mean}|$ wherein $\phi_{min}$ is the minimum value of the porosity $\phi$, $\phi_{max}$ is the maximum value of the porosity $\phi$; and, $\phi_{mean}$ is the mean value of the porosity statistical distribution function $F(\phi)$ fixed as the measured porosity $\phi_{ms}$;
- provide the porosity statistical distribution function $F(\phi)$ as the symmetric function of the statistical density function $f(\rho)$ of the value $\rho$, scaled and shifted such as:

$$\frac{\Delta \phi_2}{\Delta \phi_1} = \frac{\Delta CT_1}{\Delta CT_2}$$

Figure 3B:
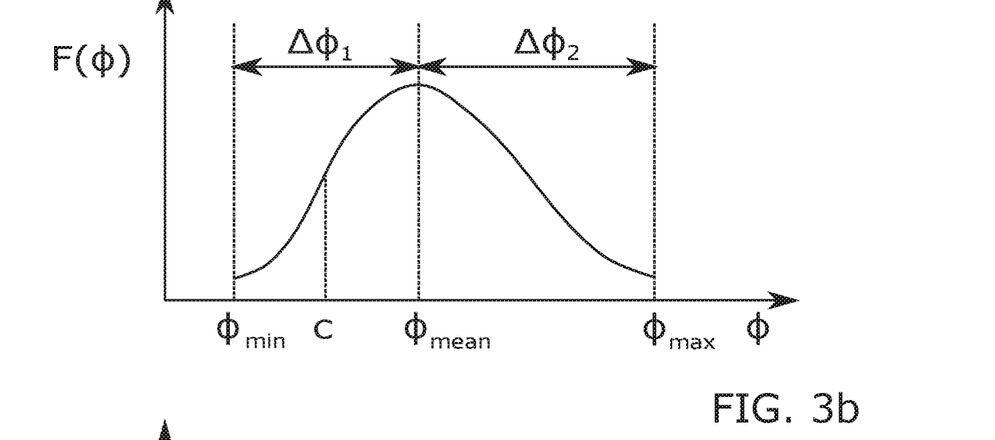

Under this condition, and as it is shown in FIGS. 3a and 3b, the porosity statistical distribution function $F(\phi)$ is the statistical density function $f(\rho)$ after being flipped according to a vertical axis and properly scaled according to the former relationship $\Delta \phi_2/\Delta \phi_1 = \Delta CT_1/\Delta CT_2$. Once all the values are known the curve is normalized between $\phi_{min}$ and $\phi_{max}$, these values can range [0, 1].

After determining if there are components which do not contribute to the porosity distribution, the density function $f(\rho)$, in an embodiment, a further truncated density function $f_c(\rho)$ is determined by truncation cutting-off the left tail of the function $f(\rho)$ at a pre-specified value $c \in [CT_{min} - CT_{max}]$ for the determination of the porosity statistical distribution function $F(\phi)$. The procedure explained in step e) is performed to get a distribution as in the FIG. 3c.

Figure 3C:
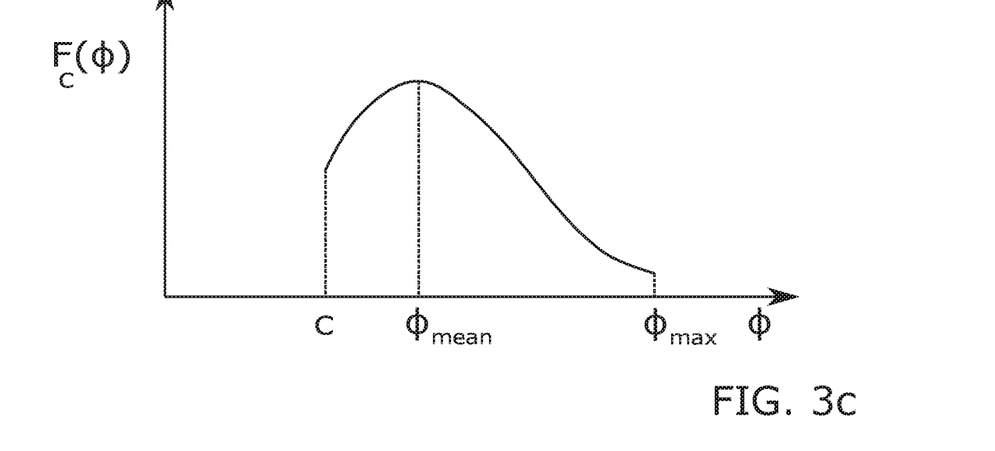

The pre-specified value c corresponds to the attenuation cut-off value identifying those components that do not contribute to the porosity of the plug sample of rock; that is, those components represented by the values located in the truncated left tail.

When populating the porosity $\phi$ in step e) of the method, according to the first aspect of the invention, said step is limited to those sub-volumes representing a component contributing to the porosity of the plug sample of rock. In the same step, the Gaussian simulation algorithm is applied as being responsive to the truncated density statistical distribution function $f_c(\rho)$. The modified porosity statistical distribution function $F(\phi)$ will be identified as the truncated porosity statistical distribution function $F_c(\phi)$. In a particular embodiment, a Gaussian simulation algorithm is implemented by using an interface comprising a pointer to a statistical distribution function for passing the function by reference. The instantiated porosity statistical distribution function $F_c(\phi)$ is allocated to said pointer in such a way the Gaussian simulation algorithm directly uses said porosity statistical distribution function $F_c(\phi)$.

Once the porosity statistical distribution function $F(\phi)$ or $F_c(\phi)$ is determined it is populated for each sub-volume of the 3D model by spatially distributing it by means of a Gaussian simulation algorithm responsive to said porosity statistical distribution function ($F(\phi)$ or $F_c(\phi)$).

The permeability k is deemed to depend on the porosity $\phi$ according to a continuous function $k(\phi)$, so the permeability is populated for each cell of the sub-volume responsive to the porosity already calculated, that is, the permeability is obtained as responsive to the porosity according to a predetermined function $k(\phi)$.

The proposal of the 3D numerical model obtained is numerically simulated according to the same conditions used in the laboratory for measuring the porosity and the permeability. Said simulations provide the calculated porosity and the calculated permeability.

If the difference between the calculated and the measured properties are less than a pre-specified threshold then the proposed 3D model is deemed to be valid. If not, the porosity and the permeability is recalculated as disclosed wherein the process of generating a new scalar field for the porosity and permeability is iteratively repeated until the calculated porosity and the calculated permeability differ less than the pre-specified threshold.

This iterative method may converge very slowly or even not converge. If this is the case, before generating a new porosity and permeability property for the discretized domain the domain is reclustered trying a different cluster.

From the computed statistical density function $F(\phi)$, a truncated function $F_c(\phi)$ is proposed as the probability density function of the porosity. Another variable used for avoiding the slow convergence is the cut-off c value of the attenuation. These criteria, the cut-off value c or the clustering, may be recalculated if the iterations carried out generating the porosity and the permeability are more than a pre-specified value.

Once the method has converged, the 3D numerical model reproduces the porosity and the permeability of the plug for the $\phi_{ms}$ and the $k_{ms}$ measurements.

The method further comprises additional checks in the connectivity of the components that contribute to the porosity of the plug sample of rock by further comprising:
measuring the permeability $k_{ms}(s)$ of the plug sample of rock by an experiment with two fluids, depending on the saturation s of one fluid in respect to the other fluid for a pre-specified range of the s variable,
the numerical simulation according to step g) is extended to provide the numerical values of the permeability $k_{num}(s)$ for at least the same range of the s variable,
the condition of the iterative process in step h) is further limited to the condition that the global permeability measured on the plug sample of rock $k_{ms}(s)$ and the permeability $k_{num}(s)$ calculated from the 3D model differ less than a pre-specified threshold for the range of the s variable measured under a pre-specified norm.

The use of two fluids ranging with different values of the saturation s of one fluid in respect to the other fluid provides a function representing the permeability $k_{ms}(s)$ in the range of s being measured.

The iterative process applied has a stricter criterion as the permeability of the numerical model must fulfill the measurements in a range of the saturation variable, not only in just one value.

The 3D model obtained for the plug will be used as the basis for generating the corresponding facies of the 3D model of the large sample of rock, the core. If the same resolution of the plug is used in the 3D model of the large sample, the discretization for the core would be too large.

The size of the sample of rock taken from this well is usually quite large and the generation of a 3D numerical model for it may require a computational cost that may be non-affordable.

In this embodiment, according to the 3D numerical model of the plug sample taken from the core or sample of rock (2) before stochastically populating to the cell discretization of the second 3D numerical model from the cell discretization of the first 3D numerical model of the plug sample of rock, said cell discretization of the plug sample of rock is coarsened in order to reduce its discretization size.

The method, when including the coarsening of the cell discretization of the plug sample of rock, comprises:
generating a coarser cell discretization than the cell discretization of the plug wherein each cell of the coarser discretization comprises one or more cells of the cell discretization of the plug sample of rock,
each cell of the coarser discretization comprises the component with higher frequency among the components of the cell discretization of the plug sample of rock,
the density of each cell of the coarser discretization is calculated as the mean of the density among the cells of the cell discretization of the plug sample of rock, the porosity of each cell of the coarser discretization is calculated as the mean of the porosity among the cells of the cell discretization of the plug sample of rock, the permeability of each cell of the coarser discretization is calculated as k($\phi$) from the porosity $\phi$ value at said cell of the coarser discretization, make available the coarser cell discretization as the new discretization of the plug sample of rock to be used in the Multipoint Statistics (MPS) algorithm.

The coarsened 3D numerical model is used as training images to propagate the spatial component structure at core scale. Using Gaussian simulation methods the porosity is populated as a function of the components and respecting the experimental results. The permeability is estimated according to a continuous function k($\phi$). The 3D numerical model provides a pattern of the internal structure of the components and the components itself that is propagated along a bigger structure such as the core.

As a summary, a method for providing a 3D numerical model of the sample of rock taken from a vertical portion of the core extracted from a well of an oil or gas reservoir is proposed according to an embodiment of the invention, this method comprises the following steps:

carrying out a CT scan of the sample of rock, identifying the facies and the number of components of the facies of the sample of rock, for each facies,
  extracting a plug sample of rock from said facies of the sample of rock,
  generating a first 3D numerical model for the plug sample of rock according to the first aspect of the invention, at least comprising a cell discretization representing the volume of said plug sample of rock, generating a second 3D numerical model, at least comprising a cell discretization representing the volume of the sample of rock, taken as the longitudinal portion of the core, wherein the volume of the sample of rock comprises the volumes of the plugs and wherein:

the cell discretization of the second 3D numerical model is clustered according to the facies of the 3D sample, for each cluster representing a facies, the components are stochastically populated to the cell discretization of said second 3D numerical model by means of a MPS algorithm (Multipoint Statistics) responsive to the patterns provided by the cell discretization of the plug sample of rock of the first 3D model of its facies and restricted to the condition that the number of components n of the sample of rock and the partial rate for each component $f_i$, i=1 . . . n is kept, for each cluster representing a facies, the porosity are stochastically populated to the cell discretization of said second 3D numerical model by means of a Gaussian algorithm, for each cluster representing a facies, the permeability is populated among the cells as an scalar function responsive of the porosity of second 3D numerical model k($\phi$), making the second 3D numerical model available.

Therefore, the proposed method generates a 3D numerical model of the sample of rock in two steps:

first generating 3D numerical models of plug samples of rock taken from each facies of the sample of rock, wherein the 3D numerical model of each plug is quite smaller than the size of the sample of rock; and second generating the 3D numerical model of the entire sample of rock populating data from the 3D models of the plug corresponding to each facies while keeping two constraints: the number of components of the sample of the rock and the partial rate for each component is kept.

The 3D numerical model of the sample of rock (2) taken from the well (1) generated as disclosed reproduces the porosity and the permeability as it has been generated propagating the patterns of the individual 3D models of each plug sample taken for each corresponding facies.

Nonetheless, the 3D numerical model may no reproduce the dynamical behavior of the sample of rock. If this is the case, the developed models are dynamically simulated to validate laboratory results and, if not, the method is iteratively carried out until it is validated.

In this case, when a plurality of patterns taken from the 3D numerical model of the plug are populated within the discretization of the large 3D model of the sample of rock, the combination of patterns provide flow paths that shows dynamical properties that may differ from those measured in the sample of rock (2) extracted from the well (1). These paths are randomly regenerated when the plurality of patterns are statistically propagated. The 3D numerical model of the core or sample of rock (2) is generated as many times as needed to reach the convergence of the iterative method.

According to a preferred embodiment, a plurality of 3D models generated as disclosed and, iteratively compared with the measurements of the samples of rock for a range of the saturation variable.

According to an embodiment, the comparison is as follows:

i) in a first step the simulation of the fluid flow over the 3D numerical model at a specific saturation generates a relative permeability value;

ii) this relative permeability value is compared with the value of the experiment measured under the same conditions;

iii) If the 3D model shows a permeability value (flow properties) differing less than a predetermined threshold, the permeability value is kept;

iv) otherwise the permeability is modified by repeating from i) to iii).

In this case, the validated 3D model will be that showing flow properties that differ less than a predetermined threshold measured for the entire range.

The method further comprises any calculation of the porosity, the permeability or both in a plurality of sections along the longitudinal direction of the second 3D numerical model providing one or more discrete functions.

The invention claimed is:

1. A method for providing a numerical model of a sample of rock, in particular a plug sample taken from a sample of rock, said sample of rock taken from a vertical portion of the rock core, according to its longitudinal direction, extracted from a well of an oil or gas reservoir, the method comprising:

performing a CT scan of the plug sample of rock;
  measuring a porosity $\phi_{ms}$ of the plug sample of rock;
  measuring a permeability $k_{ms}$ of the plug sample of rock;
  generating a 3D numerical model, at least comprising a cell discretization representing a volume of the plug sample of rock, according to the following steps:
    a) recovering data from the CT scan providing at least information on a statistical density function $f(\rho)$ of the value $\rho$, wherein $\rho$ is an attenuation X-ray radiation in the volume of the plug sample of rock;
    b) generating a segmentation of the discretization of the first 3D model into sub-volumes responsive to the data retrieved in step a) from the plug sample of rock, said sub-volumes representing components of the plug sample of rock;

c) identifying the components of each sub-volumes;

d) determining a porosity statistical distribution function $F(\phi)$ for the cells of the 3D model at least responsive to the statistical density function $f(\rho)$;

e) populating a porosity $\phi$ for each sub-volume of the 3D model, wherein the porosity is spatially distributed among the cells of said sub-volume by means of a Gaussian simulation algorithm responsive to the porosity statistical distribution function $F(\phi)$ as an approximation of a Gaussian density function;

f) populating a permeability among the cells of each sub-volume comprising a component contributing to the porosity, wherein the permeability is defined as a scalar function responsive to the porosity of the cell $k(\phi)$;

g) performing a numerical simulation of the 3D model according to conditions relating to the permeability $k_{ms}$ order to obtain a global permeability $k_{num}$;

h) iteratively repeating steps e) to g) until the global permeability measured on the plug sample of rock $k_{ms}$ and the permeability $k_{num}$ calculated from the 3D model differ less than a threshold.

2. The method according to claim 1, wherein the porosity statistical distribution function $F(\phi)$ at step d) is determined as follows:

determining $\Delta CT_1=|CT_{mean}-CT_{min}|$ and $\Delta CT_2=|CT_{max}-CT_{mean}|$ as the $\rho$ values ranges from $CT_{min}$ to $CT_{max}$, and the statistical density function $f(\rho)$ has a mean value at $CT_{mean}$;

being $\Delta\phi_1=|\phi_{mean}-\phi_{min}|$ and $\Delta\phi_2=|\phi_{max}-\phi_{mean}|$ wherein $\phi_{min}$ is a minimum value of the porosity $\phi$, $\phi_{max}$ is a maximum value of the porosity $\phi$; and, $\phi_{mean}$ is a mean value of the porosity statistical distribution function $F(\phi)$ fixed as the measured porosity $\phi_{ms}$;

provide the porosity statistical distribution function $F(\phi)$ as a symmetric function of the statistical density function $f(\rho)$ of the value $\rho$, scaled and shifted according to:

$$\frac{\Delta\phi_2}{\Delta\phi_1} = \frac{\Delta CT_1}{\Delta CT_2}$$

3. The method according to claim 1, wherein for determining the porosity statistical distribution function $F(\phi)$ on step d), the density function $f(\rho)$ is further truncated as $f_c(\rho)$ by cutting-off a left tail of the density function $f(\rho)$ at a pre-specified value $c\in[\phi_{min}, \phi_{max}]$ providing a truncated porosity statistical distribution function $F_c(\phi)$ corresponding to the porosity values of those components that do not contribute to the porosity of the plug sample of rock; and, when populating the porosity $\phi$ in step e), said step is limited to those sub-volumes representing a component contributing to the porosity of the plug sample of rock and the Gaussian simulation algorithm is responsive to the truncated porosity statistical distribution function $F_x(\phi)$.

4. The method according to claim 1, wherein step h), when the global permeability measured on the plug sample of rock $k_{ms}$ and the permeability $k_{num}$ calculated from the 3D model differs more than the threshold, before repeating steps e) to g) step h) further comprises truncating the porosity statistical distribution function by specifying a new value of $c\in[\phi_{min},\phi_{max}]$.

5. The method according to claim 1, wherein the Gaussian simulation algorithm of step e) is a sequential Gaussian simulation algorithm.

6. The method according to claim 1, wherein the Gaussian simulation algorithm of step e) is a Gaussian random function simulation algorithm.

7. The method according to claim 1, wherein a first porosity statistical distribution function $F(\phi)$ responsive to the statistical density function $f(\rho)$ in step d), when represented within a normalized range [0,1], is calculated as:

measuring a mean porosity $\phi_{mean}$ from the plug sample of rock according to:

$$\frac{\Delta CT_2}{\Delta CT_1} = \frac{\Delta\phi_1}{\Delta\phi_2}$$

8. The method according to claim 1, further including evaluating a connectivity of the components contributing to the porosity of the plug sample of rock by:

measuring a permeability $k_{ms}(s)$ of the plug sample of rock using two fluids, based on a saturation s of one fluid with respect to the other fluid for a specified range of the s variable;

performing a numerical simulation according to step g) that further provides the numerical values of the permeability $k_{num}(s)$ for at least the specified range of the s variable; and iteratively repeating steps e) to g) according to step h) until the global permeability measured on the plug sample of rock $k_{ms}(s)$ and the permeability $k_{num}(s)$ calculated from the 3D model differ less than the specified threshold for the range of the s variable measured under a specified norm.

9. The method for providing a 3D numerical model of the sample of rock taken from a vertical portion of the core extracted from a well of an oil or gas reservoir, comprising:

performing a CT scan of the sample of rock;

identifying facies and a number of components of the facies of the sample of rock;

for each facies, extracting a plug sample of rock from said facies of the sample of rock;

generating a first 3D numerical model according to claim 1, at least comprising a cell discretization representing a volume of the plug sample of rock;

generating a second 3D numerical model, at least comprising a cell discretization representing a volume of the sample of rock, taken as a longitudinal portion of the rock core, wherein the volume of the sample of rock comprises the volumes of the plugs and the cell discretization of the second 3D numerical model is clustered according to the facies of the 3D sample;

for each cluster representing a facies, the components are stochastically populated to the cell discretization of said second 3D numerical model by means of a MPS algorithm (Multipoint Statistics) responsive to patterns provided by the cell discretization of the plug sample of rock of the first 3D model of its facies and restricted to a condition that the number of components n of the sample of rock and the partial rate for each component $f_i$ i=1 . . . n is maintained;

for each cluster representing a facies, the porosity are stochastically populated to the cell discretization of said second 3D numerical model by means of a Gaussian algorithm;

for each cluster representing a facies, the permeability is populated among the cells as a scalar function responsive to the porosity of second 3D numerical model $k(\phi)$.

10. The method according to claim 9, wherein before stochastically populating to the cell discretization of the second 3D numerical model from the cell discretization of the first 3D numerical model of the plug sample of rock, said cell discretization of the plug sample of rock is coarsened.

11. The method according to claim 10, wherein the coarsening of the cell discretization of the plug sample of rock comprises:
- generating a coarser cell discretization than the cell discretization of the plug wherein each cell of the coarser discretization comprises one or more cells of the cell discretization of the plug sample of rock;
- each cell of the coarser discretization comprises the component with higher frequency among the components of the cell discretization of the plug sample of rock;
- a density of each cell of the coarser discretization is calculated as a mean of the density among the cells of the cell discretization of the plug sample of rock;
- a porosity of each cell of the coarser discretization is calculated as a mean of the porosity among the cells of the cell discretization of the plug sample of rock;
- a permeability of each cell of the coarser discretization is calculated as $k(\phi)$ from the porosity $\phi$ value at said cell of the coarser discretization;
- provide the coarser cell discretization as a new discretization of the plug sample of rock to be used in the MPS algorithm.

12. The method according to claim 9, wherein the porosity, the permeability, or both, are calculated in a plurality of sections along the longitudinal direction of the second 3D numerical model providing one or more discrete functions.

13. A computer program product adapted to carry out a method according to claim 1.

* * * * *